United States Patent [19]

Shimada et al.

[11] Patent Number: 4,762,889

[45] Date of Patent: Aug. 9, 1988

[54] WATER ABSORPTIVE RESIN COMPOSITIONS AND PROCESS FOR PRODUCING THE SAME

[75] Inventors: Takeo Shimada; Noriyuki Okada; Takashi Fujimoto; Shuhei Yada, all of Yokkaichi, Japan

[73] Assignee: Mitsubishi Petrochemical Company Limited, Tokyo, Japan

[21] Appl. No.: 865,050

[22] Filed: May 20, 1986

[30] Foreign Application Priority Data

May 20, 1985 [JP] Japan ................................ 60-107942

[51] Int. Cl.[4] .................... C08L 33/02; C08L 43/00
[52] U.S. Cl. .................................. 525/201; 525/208
[58] Field of Search ............................. 525/201, 208

[56] References Cited

FOREIGN PATENT DOCUMENTS

| | | | |
|---|---|---|---|
| 0560331 | 7/1958 | Canada ................................ | 525/201 |
| 0168139 | 1/1986 | European Pat. Off. ............ | 525/208 |
| 58-45245 | 3/1983 | Japan ................................. | 525/208 |
| 58-129039 | 8/1983 | Japan ................................. | 525/208 |
| 59-58048 | 4/1984 | Japan ................................. | 525/208 |

*Primary Examiner*—John C. Bleutge
*Assistant Examiner*—Robert E. L. Sellers, II
*Attorney, Agent, or Firm*—Robert E. Burns; Emmanuel J. Lobato

[57] ABSTRACT

The water absorptive resin composition of this invention is a composite comprising 5 to 95% of a carboxylate-containing water absorptive resin and 95 to 5% of a glycidyl group-containing polyolefin. The process for producing this water absorptive resin composition according to this invention comprises kneading a carboxylate-containing water absorptive resin and a glycidyl group-containing polyolefin under the kneading conditions of a kneading temperature of 120° to 280° C. and a residence time in a kneader of 2 seconds or more. According to this invention, there is produced a composition of excellent water absorptivity, shape maintenance and moldability into a film.

5 Claims, No Drawings

WATER ABSORPTIVE RESIN COMPOSITIONS AND PROCESS FOR PRODUCING THE SAME

BACKGROUND OF THE INVENTION

This invention relates to novel water absorptive resins which have high water absorptivity and are capable of retaining their shape after absorption of water and of being molded into a variety of forms such as film, fiber and molded materials.

Water absorptive resins are used for many applications as absorbent materials for hygienic media such as paper diapers, sanitary napkins, water retentive agents for agriculture and gardening, and other industrial materials.

Resins currently available as water absorptive resins are crosslinked alkali metal salts of polyacrylic acid, crosslinked products of alkali metal acrylate grafted starch, crosslinked copolymers of vinyl alcohol and alkali salts of acrylic acid, crosslinked copolymers of vinyl alcohol-maleic anhydride, and the like. Each of these resins has a crosslinking structure for sustaining its shape after absorption of water.

The use of the water absorptive resins has recently become widespread, and furthermore the water absorptive resins are increasingly required to have shapes in use of not only powder but also film, fiber and molded articles.

However, the currently available water absorptive resins are crosslinked products and thus are not thermoplastic, so that it is difficult to form them into film or fiber. Furthermore, even if films can be obtained by compression molding, such products may be disadvantageous because of their low impact strength.

There have been many researches on water absorptive resins which are capable of being molded into film or fiber in order to solve the above problem. But most of their results have been unsatisfactorily. For instance, the method wherein a thermoplastic resin of excellent moldability such as polyethylene, polypropylene or the like is blended with a carboxylate-containing water absorptive resin afforded no uniform dispersions because of poor compatibility of the thermoplastic resin with the water absorptive resin. Accordingly, researches were conducted on the blending of a water absorptive resin with a polar group-containing thermoplastic resin, which is recognized to have a good affinity with the water absorptive resin. Polar group-containing thermoplastic resins such as an ethylene-vinyl acetate copolymer (EVA), an ethylene-ethyl acrylate copolymer (EEA) and an ethylene-acrylic acid copolymer (EAA) exhibited excellent compatibility with carboxylate-containing water absorptive resins and produced uniform dispersions, but the dispersions were inferior in water absorption property and poor in shape maintenance after absorption of water. They also have the problem of peeling off of the water absorptive resin.

SUMMARY OF THE INVENTION

In view of these present circumstances, we have conducted researches in order to develop a water absorptive resin which can be molded into film or fiber. As a result, we have found that the combination of a water absorptive resin with a reactive thermoplastic resin which shows polymer reaction together with the former resin gives a water absorptive resin satisfying all of the properties such as high water absorptivity, shape maintenance and modability and thus have achieved the present invention.

More specifically, the water absorptive resin composition according to this invention is characterized by a composite material comprising 95 to 5% of a carboxylate-containing water absorptive resin and 5 to 95% of a glycidyl group-containing polyolefin (wherein these percentages are based on the total weight of both components).

Further, the process for producing a water absorptive resin composition according to this invention is characterized by kneading a carboxylate-containing water absorptive resin and a glycidyl group-containing polyolefin under the kneading conditions of a kneading temperature of 120° to 280° C. and a residence time in a kneader of at least 2 seconds.

The water absorptive resin composition of this invention is superior to the well-known compositions mentioned above in all of the properties such as water absorptivity, shape maintenance and film moldability.

In order to ensure shape maintenance after absorption of water, it is necessary to form a certain bonding between the water absorptive resin and the resin intended to afford moldability. We have examined thermoplastic resins which show polymer reaction together with crosslinked alkali metal polyacrylates as the typical carboxylate-containing water absorptive resins and, as a result thereof, have found that only polyolefins containing a specific functional group (glycidyl group) make possible the accomplishment of the objects of this invention.

DETAILED DESCRIPTION OF THE INVENTION

Composition

The composition of this invention is a composite product of a carboxylate-containing water absorptive resin and a glycidyl group-containing polyolefin.

Carboxylate-Containing Water Absorptive Resin

A carboxylate-containing water absorptive resin suitable for use in this invention is defined as follows.

First of all, the "carboxylate" is a neutralized salt of a carboxyl group and is represented by the general formula —COOM, wherein M represents a monovalent alkali metal (Na, K, etc.) or ammonium ($NH_4$). The reaction ratio of the carboxyl group of a water absorptive resin and the alkali metal can be changed depending on the water absorptivity of the resin and is generally in the range of 40 to 100%.

From the standpoint of the possible intended uses, the carboxylate-containing water absorptive resin preferably has a water absorption in the range of about 30 to 2,000 times (water absorption will be defined hereinafter).

Representative processes for producing the water absorptive resin of this invention are disclosed in Japanese Patent Application No. 275308/84, Japanese Patent Application Laid-Open Nos. 71907/83, 62665/84 and 42602/83, and other publications.

The carboxylate-containing water absorptive resin which is appropriate for use in this invention specifically includes, e.g., crosslinked products of sodium acrylate, potassium acrylate, and lithium acrylate. The resin is preferably of crosslinked structure. The crosslinked structure can be introduced therein by copolymerizing divinyl or diacrylic compounds, particularly water soluble ones such as N,N′-methylene-bis-acrylamide, ethylene glycol bis-acrylate and the like.

Glycidyl Group Containing Polyolefin

The glycidyl group-containing polyolefin contained in the composition of this invention is defined as follows.

First of all, it may be either a backbone copolymer or a graft copolymer provided that it is a glycidyl group-containing thermoplastic polyolefin.

The backbone copolymer includes olefins, for example, a copolymer of ethylene and a glycidyl-containing monomer. Specific examples are ethylene-glycidyl acrylate copolymers, ethylene-glycidyl methacrylate copolymers, and ethylene-glycidyl crotonate copolymers. Generally, the backbone copolymer includes all of the copolymers of an olefin such as ethylene and a vinyl group epoxy compound.

The aforementioned ethylene copolymer may be a terpolymer including a third or other monomer that has been copolymerized for the purpose of affording the properties such as flexibility and the like. The monomer which may be used as the third or other comonomer includes all of the monomers copolymerizable with ethylene. Examples are vinyl esters such as vinyl acetate, vinyl propionate, and acrylic acid esters such as methyl acrylate, ethyl acrylate, butyl acrylate, and octyl acrylate, methacrylic acid esters such as methyl methacrylate and ethyl methacrylate, and halogenated vinyl such as vinyl chloride and vinyl fluoride.

The graft copolymer includes grafted products of a gylcidyl-containing monomer to polyethylene, polypropylene, polybutene, and polymethylpentene. The monomers used for grafting specifically includes glycidyl acrylate, glycidyl methacrylate, glycidyl crotonate, and vinyl glycidyl.

Throughout the following description, quantities expressed in precent (%) or "parts" are by weight.

The glycidyl content of such glycidyl-containing polyolefins is preferably 0.1 to 20%. If the glycidyl content is less than 0.1%, there is a great possibility of the shape maintenance after absorption of water being insufficient. On the other hand, if the glycidyl content exceeds 20%, the polyolefin will tend to form a gel, thus losing moldability. The glycidyl content is preferably 0.5 to 15%, more preferably 1 to 10% by weight.

The glycidyl group-containing polyolefin is required to have a molecular weight of at least a certain level in order that it can be molded into film or fiber. Specifically, the molecular weight is preferably 5,000 or more of a number average molecular weight based on GPC.

The aforementioned third or other comonomer used in the copolymer of three-way or more, such as a terpolymer, can be introduced in a proportion of 0 to 50% to the total weight of the copolymer provided that the copolymer will not result in restrictions on properties such as strength, and melting point.

The shape of the glycidyl group-containing polyolefin may be either powder or pellet, but it is desirably a powder for dispersing quality.

Compounding Ratio

The composition of this invention comprises 95 to 5% of a carboxylate-containing water absorptive resin and 5 to 95% of a glycidyl-containing polyolefin (the % being based on the total weight of the two). If the content of the carboxylate-containing water absorptive resin exceeds 95%, the moldability will deteriorate. If it is less than 5%, the water absorbing capacity will be low, thus losing the superiority obtained by using the composition as a film or fiber having water absorptivity. The compounding ratio is preferably 30 to 90% of the former water absorptive resin and 70 to 10% of the latter polyolefin.

The optimum compounding ratio of the carboxylate-containing water absorptive resin and the glycidyl group-containing polyolefin varies depending on the intended uses of the composition. In general, it is preferable that the content of the carboxylate-containing water absorptive resin be increased for uses wherein water absorptivity is important, and the content of the glycidyl group-containing polyolefin is increased for uses wherein importance is placed on moldability.

Structure of the Composition and Miscellaneous Properties

The composite compound of the above two components to construct the water absorptive resin composition according to this invention is not a simple mixture of the two components but is presumably composed by at least a partial reaction of the two. The reaction in this case is presumed to occur between the carboxylate group and the glycidyl group.

The composition of this invention is included in the scope of a thermoplastic resin, so that it can be used in the fashion that is usually used in such a resin material by blending with other themoplastic resins, e.g., polyethylene, polypropylene, and ethylene-vinyl acetate copolymers, and it can also be used by blending therewith an oil resin, a wax, a stabilizer, an antistatic agent, an ultraviolet ray absorber, a synthetic rubber, a natural rubber, a lubricating agent, an inorganic filler, etc. These ancillary materials can be caused to be present during the process of forming the composite product by the melt kneading of the aforementioned essential two components, they can be added after the composite product has been formed.

Uses

The water absorptive resin composition of this invention shows the aforementioned excellent effects and thus can be applied to a variety of uses. It is typically applied in a form such as a fiber, a film, a sheet, a composite fiber, film or sheet thereof with other polyolefins or various materials to a condensation resistant agent, a wall paper material, an interior material, a food packaging material, a drug packaging material, a water retentive agent for agriculture and gardening, and a hygienic medium, and thus it can be applied to a great variety of fields. It can be also processed into a layered product.

Preparation of the Composition

The composite formation of the carboxylate-containing water absorptive resin and the glycidyl group-containing polyolefin is conducted by melt kneading at the melting point of the glycidyl group-containing polyolefin or higher temperature.

The kneader used for the melt kneading may be the one which is conventionally used in the kneading of thermoplastic resins. Specifically, it includes, for example, a double-shaft kneader such as a Brabender Plastograph, CIM, FCM and the like single-shaft extruder, etc.

The process for producing the composition is specifically defined as follows. The kneading temperature is generally 120° to 280° C., and the optimum temperature is preferably 130° to 250° C., although it varies depending on the kinds of the glycidyl group-containing polyolefin and the carboxylate-containing water absorptive resin. If the kneading temperature is less than 120° C., the graft reaction of both components will not be satisfactorily conducted. On the other hand, if it exceeds 280° C., part of the glycidyl-containing polyolefin or the carboxylate-containing absorptive resin will deteriorate during kneading. The residence time in the kneader is 2 seconds or more, preferably at least 3 seconds. If the residence time in the kneader is less than 2 seconds, a satisfactory water absorptive resin composition cannot be produced.

EXPERIMENTAL EXAMPLES

Measurements used for the evaluation of the composition of this invention are as follows.
(1) Molecular weight: in accordance with the GPC method
(2) Water absorption: (water absorption of the water absorptive resin)

To a one liter breaker are added approximately 0.5 g of a polymer and approximately 1 liter of pure water. The mixture is agitated and then allowed to stand for approximately 60 min. thus causing the polymer to swell with water. After hydro-extraction through a 100 mesh screen, the filtrate is weighed and the pure water absorbing capacity is calculated according to the following equation.

$$\text{Water absorption} = \frac{\text{Weight of charged water (g)} - \text{Weight of filtrate (g)}}{\text{Weight of charged polymer (g)}}$$

(Water absorption of the water absorptive resin composition)

To a one liter-volume beaker are added approximately 1 g of the water absorptive resin composition and approximately 1 liter of pure water, and the mixture is left standing for approximately 24 hours to cause the composition to swell amply. Then the mixture is drained with a 8 mesh screen, and the water adhering to the surface of the polymer is removed with a filter paper, after which the polymer is weighed. Calculation of the water absorption is conducted by using the following equation.

$$\frac{\text{Water}}{\text{absorption}} = \frac{\text{Weight of polymer after absorbing water (g)}}{\text{Weight of charged polymer (g)}}$$

(3) Content of comonomer: in accordance with NMR method
(4) Shape maintenance: in accordance with visual observation after absorption of water The forming of an inflation film was conducted with a 50 $\psi$ extruder (mfd. by Mitsubishi Heavy Industries, Ltd.)

EXAMPLE 1

As a carboxylate-containing water absorptive resin, a cross-linked sodium polyacrylate was prepared in accordance with the method disclosed in the specification of Japanese Patent Application No. 275308/84. The crosslinked sodium polyacrylate thus obtained was the one wherein the crosslinking structure had been formed by adding N,N$^{31}$-methylene-bisacrylamide as a crosslinking agent in a proportion of 0.05% to polyacrylic acid. The saponificatin ratio using NaOH was 70%, and the water absorption was 780 times.

The crosslinked sodium polyacrylate (50 parts) and an ethylene-methyl acrylate-glycidyl methacrylate terpolymer (50 parts) were kneaded in a biaxial kneader FCM at a temperature of 150° C. for 3 seconds.

The ethylene-methyl acrylate-glycidyl methacrylate terpolymer used was the one wherein the contents of methyl acrylate and glycidyl methacrylate were respectively 10% and 4%, and the number average molecular weight was 15,000.

The water absorptive resin composition thus obtained was capable of being molded into a cast film. On testing the film obtained with respect to water absorptivity, the water absorption was 85 times. The shape maintenance after water absorption was good, and no removal of the crosslinked sodium polyacrylate was observed.

EXAMPLE 2

The crosslinked sodium polyacrylate (50 parts) used in Example 1 and an ethylene-vinyl acetate-glycidyl methacrylate terpolymer (50 parts) were kneaded in a double-shaft kneader FCM at 170° C. for 3 seconds. The ethylene-vinyl acetate-glycidyl methacrylate terpolymer was the one wherein the contents of vinyl acetate and glycidyl methacrylate were respectively 8% and 2% and the number average molecular weight was 18,000.

The water absorptive resin composition thus obtained was capable of being molded into a cast film. On testing the film obtained with reference to water absorptivity, the water absorbing ratio was 80 times. The shape maintenance after water absorption was good, and no removal of the crosslinked sodium polyacrylate was observed.

COMPARATIVE EXAMPLE 1

The crosslinked sodium polyacrylate (50 parts) used in Example 1 and an ethylene-acrylic acid copolymer (50 parts) were kneaded in a double-shaft kneader FCM at 150° C. for 3 seconds. The ethylene-acrylic acid copolymer used was one wherein the content of acrylic acid was 8%, and the number average molecular weight was 22,000.

The water absorptive resin thus obtained was capable of being molded into a cast film as in Example 1. But after water absorption, the crosslinked sodium polyacrylate was dissolved into the water and the shape could not be maintained. The apparent water absorbing ratio which excludes the weight of crosslinked sodium polyacrylate which has dissolved into the water was 2 times.

EXAMPLE 3

Commercially available AQUAKEEP/OSH (20 parts mfd. by SEITETSU KAGAKU Co., Ltd.) and the ethylene-methyl acrylate-glycidyl methacrylate terpolymer (80 parts) used in Example 1 were kneaded in a double-shaft kneader FCM at a temperature of 150° C. for 3 seconds. The water absorptive resin composition thus obtained was capable of being molded into a cast film. On testing the film thus obtained with respect to water absorptivity, the water absorption was found to be 9 times. The shape maintenance after water absorption was good, and no removal of the AQUAKEEP was observed.

AQUAKEEP/OSH is a carboxylate-containing water absorptive resin.

COMPARATIVE EXAMPLE 2

The AQUAKEEP/OSH (50 parts) used in Example 3 and an ethylene-acrylic acid copolymer (50 parts) were kneaded in a biaxial kneader FCM at a temperature of 150° C. for 3 seconds. The water absorptive resin thus obtained was capable of being molded into a cast film. However, after water absorption the AQUAKEEP was dissolved in the water, and the shape could not be maintained. The apparent water absorption which excludes the weight of the AQUAKEEP which had dissolved in water was 0.6 times.

What is claimed is:

1. A water absorptive resin composition which is a composite material comprising 95 to 5% of a crosslinked carboxylate-containing water absorptive resin and 5 to 95% of a glycidyl group-containing polyolefin, wherein the percentages are based on the total weight of both components, said carboxylate-containing water absorptive resin being an alkali metal salt of a crosslinked polyacrylic acid in which 40 to 100% of carboxyl groups have been converted into carboxylate groups, said crosslinked polyacrylic acid consisting essentially of acrylic acid and a copolymerizable crosslinking monomer selected from the group consisting of divinyl compounds and diacrylic compounds, said glycidyl group-containing polyolefin having a glycidyl content of 0.1 to 20% by weight, and said composite material being produced by the process comprising melt kneading the alkali metal salt of the crosslinked polyacrylic acid and the glycidyl group-containing polyolefin at the melting point of the glycidyl group-containing polyolefin or higher temperature.

2. A water absorptive composition resin according to claim 1 wherein the glycidyl content in the glycidyl group-containing polyolefin is 0.5 to 15% by weight.

3. A water absorptive composition resin according to claim 1 wherein the glycidyl content in the glycidyl group-containing polyolefin is 1 to 10% by weight.

4. A water absorptive composition resin according to claim 1 wherein the glycidyl group-containing polyolefin is a glycidyl group-containing ethylene copolymer.

5. A water absorptive composition resin according to claim 1 which is a composite comprising 30 to 90% by weight of a carboxylate-containing water absorptive resin and 70 to 10% by weight of a glycidyl group-containing polyolefin.

* * * * *